United States Patent [19]

McNally et al.

[11] Patent Number: 5,149,621

[45] Date of Patent: Sep. 22, 1992

[54] KIT FOR CRYOPRESERVING BLOOD VESSELS

[75] Inventors: Robert T. McNally; Cameron McCaa; Kelvin G. M. Brockbank; Albert E. Heacox, all of Marietta, Ga.; Harvey L. Bank, Charleston, S.C.

[73] Assignee: CryoLife, Inc. & Medical Univ. of South Carolina, Marietta, Ga.

[21] Appl. No.: 436,364

[22] Filed: Jan. 23, 1990

Related U.S. Application Data

[62] Division of Ser. No. 88,092, Aug. 21, 1987.

[51] Int. Cl.$^5$ ............................................... A01N 1/02
[52] U.S. Cl. ................................................ 435/1; 62/64; 623/12
[58] Field of Search ............................................. 435/1

[56] References Cited

U.S. PATENT DOCUMENTS 4,959,319 9/1990 Skelnik et al. ................. 435/240.23

OTHER PUBLICATIONS

Mueller-Schweinitzer-Chem. Abst. vol. 104 (1986) 145020g.

*Primary Examiner*—Sam Rosen
*Attorney, Agent, or Firm*—Cushman, Darby & Cushman

[57] ABSTRACT

A device for use in cryopreservation of blood vessels comprising a pair of stylets insertable into the ends of a dissected blood vessel segment. The stylets are mountable on a support track whereby the blood vessel can be distended and supported during cryopreservation procedures. Also disclosed is a freezing and thawing profile capable of maximizing endothelial cell survival. The use of chondroitin sulfate or similar compound is discussed as a novel cryoprotectant and DMSO is disclosed as a penetrating cyroprotectant.

4 Claims, 2 Drawing Sheets

KIT FOR CRYOPRESERVING BLOOD VESSELS

This is a division, of application Ser. No. 088,092, filed Aug. 21, 1987.

TECHNICAL FIELD

The present invention relates to a device for stabilizing blood vessels and more particularly to a preservation procedure for use during freezing blood vessels to ultra-cold temperatures whereby the blood vessels can be preserved for extended periods of time. Also disclosed is a method utilizing the device for freezing and thawing of blood vessels. Cryopreserved blood vessels are useful for providing grafts to patients who cannot provide their own blood vessel grafts or where fresh blood vessels are unavailable.

BACKGROUND OF THE INVENTION

"Cryopreservation" is a technique for freezing and storing cellular and tissue matter such as blood vessels, which include veins and arteries, at extremely low temperatures while preserving the viability and function of the tissue. Each year, 360,000 small vessel coronary bypass "jumps" are performed in the U.S. alone. Another 100,000 peripheral vascular procedures, below the umbilicus, are also performed. Of the small vessel procedures, 15% are performed on patients who have already had a previous operation resulting in a lack of suitable available tissue or on patients who are diabetic or have a disease which renders the tissue less than adequate. Clinically, the only alternative is to use less than optimal tissue or use artificial vessels which are prone to occlusion and thus are less than ideal. Because of the successes resulting from the cryopreservation of heart valve tissue (see copending application Ser. No. 000,095 filed Jan. 2, 1987, which is incorporated by reference in its entirety herein), and to date, more than 3,000 cryopreserved valves and approximately 2,200 implants, it is the intention to expand this technology to vein and artery tissue as well. Thus, in the clinical setting, cryopreserved tissue would fill a need for the aforementioned patents and would in addition lead to less trauma for the patient and reduce surgical time and expense.

Previous attempts at the use of allograft vessels have met with a variety of problems. The primary concern was inconsistency in the method of harvest coupled with an inability to freeze and store the tissue properly until its intended use. In addition, previous investigators failed to perform the freezing process using state of the art techniques, and consequently, the viability of the tissue was low and inconsistent and resulted in early loss of patency.

Although there have been a few published reports on the cryogenic preservation of veins and arteries, there has been no published systematic examination for the cryobiological variables involved in the preservation procedure. Most investigators have simply infiltrated the vessel with dimethyl sulfoxide (DMSO) and rapidly frozen the tissue in liquid nitrogen. Several other investigators have used uncontrolled and unmeasured freezing rates. When dissected from the body, blood vessel tissue has a natural tendency to constrict. Investigations to date show that under such conditions the endothelial lining of the vessel may be denuded; therefore, if such a vessel is transplanted, it may be prone to thrombosis. Preservation of the endothelial lining of these vessels is of particular importance, because the internal endothelial lining of the blood vessels actively inhibit thrombosis. Previous studies of saphenous vein cryopreservation indicate that the major abnormality in the frozen and thawed tissue was destruction and loss of this tissue layer. A primary goal of cryopreservation of the tissue is the prevention of ice crystals which damage or destroy cellular structure. Different freezing methods are applicable to particular tissues; not all tissues are alike in their ability to withstand cryopreservation and thawing yet maintain effective viability. No investigator is known to have successfully applied this technology to the internal mammary artery or other arterial tissue.

SUMMARY OF THE INVENTION

The device of the present invention is a structure for supporting and distending a blood vessel while permitting fluids to infiltrate the vessel to facilitate cryopreservation. More particularly disclosed is a blood vessel stent for use in cryopreserving blood vessels, the stent comprising: first and second elongated stylets each having an end capable of insertion within a portion of a blood vessel from a donor; means on said stylets operative to engage the interior of the blood vessel and thereby facilitate fluid tight ligation of the blood vessel on the stylets; and support means receiving the stylets in selectively adjustable mutually confronting relation whereby the blood vessel is distended between the stylets to prevent contraction of the blood vessel, so that the stent supports the blood vessel through the stages of procurement and cryopreservation. The method of the present invention using the device involves the technique for preparation of the vessel prior to stenting, removal, shipping to the processing laboratory, processing (including freezing), thawing and dilution. A particular emphasis is made for the preservation of the endothelium (inner lining) of the vessels in addition to keeping the basic integrity of the vessel walls intact. This involves a "no touch" surgical technique coupled with vasodilation, the use of a stent, and the use of a unique freezing profile that allows veins or arteries to be frozen down to the temperature of liquid nitrogen, approximately $-196°$ C., with minimal tissue damage due to ice crystal formation or osmotic shock. The present invention also includes a thawing schedule whereby the frozen tissue can be rapidly thawed with minimal tissue damage. Vessels that are cryopreserved according to the present invention are alive when thawed and are ideally suited for replacing diseased or damaged vessels in patients who for whatever reason do not have suitable vessels for cardiac or peripheral vascular reconstruction.

Accordingly, it is an object of the present invention to provide a device and method for retrieval and handling of human or animal vein and artery tissue.

It is another object of the present invention to provide a device and method for preserving a living vessel for long periods of time.

It is yet another object of the present invention to provide a unique set of chemical constituents prior to the freezing process.

It is yet another method of the present invention to provide a device for supporting and distending a dissected blood vessel.

It is yet another object of the present invention to provide a unique cooling schedule for freezing a vessel so that the vessel cells, including the endothelium, maintain high viability after it is thawed.

It is yet another object of the present invention to provide a method for cryopreserving a human vessel which allows rapid thawing of the vessel while maintaining maximum cell viability.

It is yet another object of the present invention to provide a living vessel such that it is suitable for transplantation after long term storage at super-cold temperatures.

It is yet another object of the present invention to provide a living vessel with a specific and unique method for thawing.

These and other objects, features and advantages of the present invention will become apparent after review of the following detailed description of the disclosed embodiment and the appended claims.

DETAILED DESCRIPTION OF THE PREFERRED EMBODIMENT

Figures 1, 2:
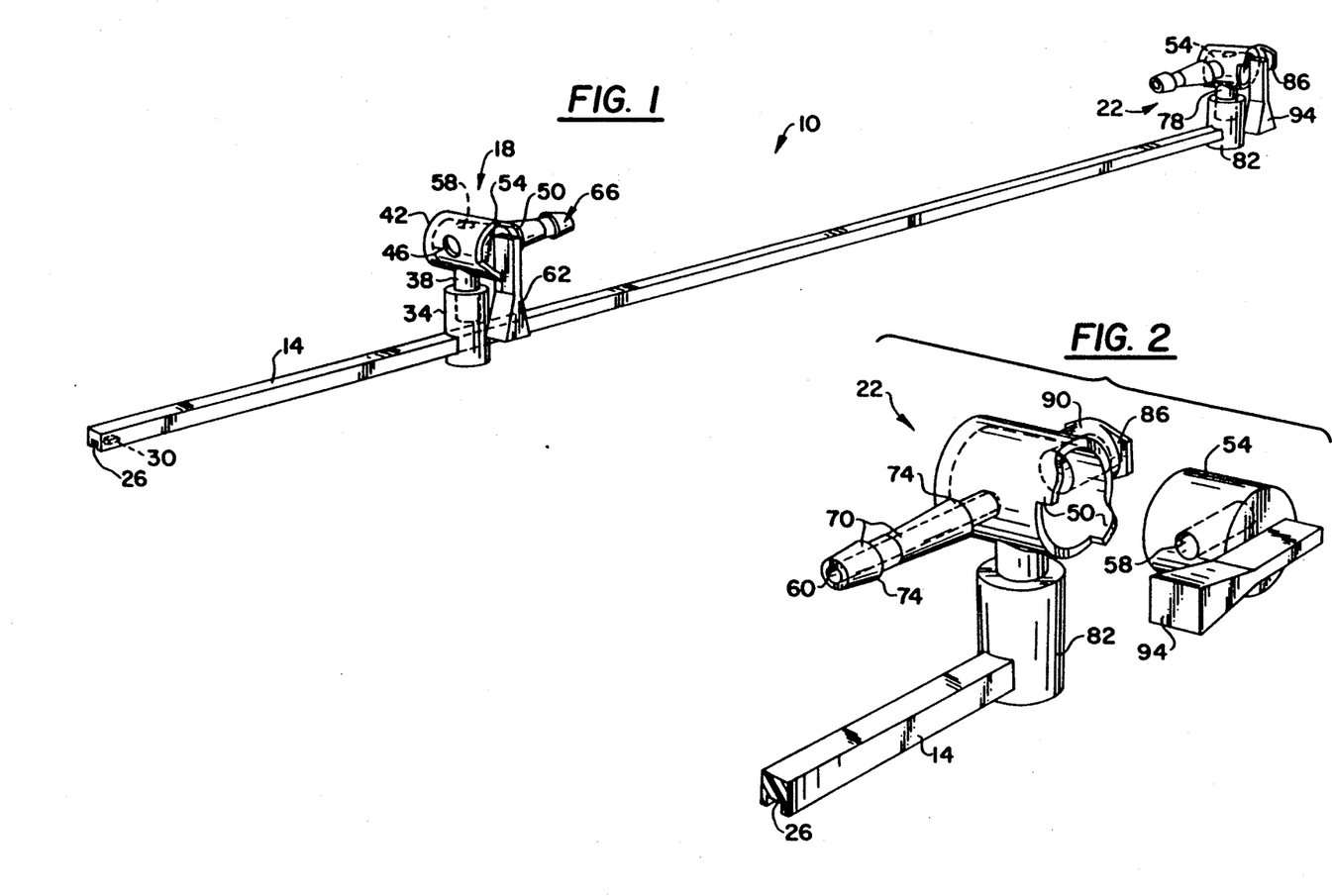
FIG. 1 is a schematic representation of a stent apparatus according to a preferred embodiment of the present invention.
FIG. 2 is an exploded isolated perspective of a stent apparatus according to a preferred embodiment of the present invention.

Referring now in more detail to the drawings, in which like numerals indicate like parts throughout the several views, FIG. 1 shows a blood vessel stent 10 which is composed of three main parts: a support track 14, sliding proximal stopcock assembly 18, and fixed distal stopcock assembly 22. All three parts can be manufactured from any appropriate material which (a) is freezable to ultra low temperatures without adverse deforming or cracking, (b) maintains flexibility at ultra low temperatures, (c) is chemically inert and will not contaminate the vessel by leaching chemicals such as plasticizers into the vessel, and (d) can withstand and not react with dimethylsulfoxide ("DMSO"), ethylene or propylene glycol, glycerol or any other chemicals or solvents used in the cryopreservation process. Track 14 is a substantially straight elongated member used to mount stopcock assemblies 18 and 22. The track can be any convenient shape, but is preferably a parallelepiped and has on one side a groove 26 running at least part of its length for the purpose of stabilizing the stopcock assemblies 18 and 22 when mounted on track 14. On the surface at the proximal end of track 14 is located a ramp 30 with a flange having its larger portion facing toward the distal end. Ramp 30 inhibits the mount from sliding off the end of track 14 once the mount is slid on the track.

Proximal slidable mount 34 is a cylindrical member having a recessed cylindrical opening axial at one end capable of matably receiving a mounting pin. At the other end of the mount 34 is an opening radial to the cylinder, capable of operatively receiving the track 14. Mount 34 is able to slide along track 14 so as to be adjustable for a given length of blood vessel segment.

Proximal stopcock assembly 18 includes a cylindrical mounting pin 38 which removably mates coaxially within the axial hole of the proximal mount 34 and is preferably able to rotate about the cylindrical axis. Pin 38 of the proximal mount is orthogonally integrated with the body 42, which is a hollow cylinder having a hole 46 extending through both sides of the cylinder, positioned orthogonal to the pin. Along one end of body 42, positioned radially opposite each other are a pair of protrusions 50 which act as stops. Stopcock barrel 54, which fits within the cylindrical interior of the body 42, is a cylinder rotatably positioned in a longitudinal orientation within body 42. A barrel hole 58 is positioned perpendicular to the barrel 54 axis through the barrel and selectively aligns with hole 46 in body 42 so as to allow a passageway through the stopcock. Lever 62 is a substantially rectangular member perpendicularly integrated with stopcock barrel 54 at one end. When rotated so that the lever is parallel with track 14, barrel hole 58 and body hole 46 are aligned to form a passageway through the stopcock while, when the barrel 54 is rotated clockwise to a position perpendicular to track 14, the holes are not in alignment, thereby blocking the passage of fluid or air through the stopcock.

Stylet 66 is a hollow substantially straight elongated tube aligned parallel to the track 14, with a port 70 at the free end of the stylet and with the other end of the stylet abutting the body 42. Stylet 66 is integrated with body 42 and is orthogonal to the pin 38. Stylet 66 is aligned with and opposite hole 46. The hollow interior of the stylet 66 communicates with the hole 46 in one side of the stopcock body 42. On the surface of stylet 66 is at least one and preferably two or more forwardly tapering ramp surfaces 70 merging with stylet 66. Stylet 66 is designed to accommodate coupling with a vessel which may be press fit upon the stylet and can abut body 42. Stylet port 68 permits fluid or air to enter the blood vessel when the stylet 66 is coupled with the blood vessel. The stylet tube is sized so as to be essentially parallel with the internal hollow bore of the tube. Ramp surface 70 terminates in a shoulder 74 which permits pressure-tight ligation as described more fully hereinbelow.

Fixed distal stopcock assembly 22 is essentially the same as sliding proximal stopcock assembly 18 except with the following notable modifications. The bore of the axial mount hole is different than that of the proximal mount hole and the diameter of the mounting pin 78 is correspondingly different from the diameter of pin 38 so that the two stopcock assemblies cannot be interchangeably mounted. This avoids confusion of which stopcock assembly is distal and which is proximal. Distal mount 82 is preferably permanently mounted on the distal end of track 14.

Distal body 86 also has integrated on its surface in alignment with the hole (as in hole 46) a Luer fitting 86 for detachably receiving a syringe. Alternatively, a hub 90 can be used without the Luer lock fitting for detectably receiving a fluid delivery device such as a syringe. Standard Luer fittings are commonly known to those skilled in the art. In an alternative embodiment a hub 90 can be integrated in a similar with the proximal stopcock assembly 18 to permit back flushing of the blood vessel before or after being mounted on track 14.

Distal lever 94 rotates in a manner similar but opposite to that of proximal lever 62; i.e., when parallel to track 14 the distal lever 94 is in the "open" position and when rotated perpendicular to the track is in the "closed" position. The stopcock levers are positioned so that when both are parallel to track 14 they point in toward each other and will not stretch the vessel during closure. In this way they do not add to the overall length of the structure, nor does the distal lever 94 interfere with distal hub or Luer fitting 86 or 90.

The stent is used to support and distend a dissected vessel. The dissection procedure is described in detail in the examples set forth hereinbelow. A specially designed perfusion solution containing a suitable vascular smooth muscle relaxant drug is applied along the length of the vessel. After a period of time, usually about 10–15 minutes, the vessel is carefully dissected using what is commonly termed as "no touch" technique, whereupon an appropriate incision is made on the distal and proximal end of the vessel. If the donor's heart is beating, the portion of the vessel which was transected will be tied with ligature. The removable stopcock assemblies 18 and 22 of stent apparatus 10 are placed one on each end of the vessel and a portion of a flushing/distention solution is perfused through the vessel. The dissection can then be completed. The perfusion medium can be any appropriate medium, preferably Delbecco's Minimal Essential Media ("DMEM"). Other media include, but are not limited to, Medium 199, Eagle media, Hank's media, Delbecco's modified Eagle media, Iscoves modified Delbecco's media, Defined media A2, CMRL-1066, RPMI-1640 (also 1603, 1630, or 1634), F10, F12, alpha media, or the like. To this media is added serum such as but not limited to human serum, fetal calf serum ("FCS"), serum substrate, or the like, and a vasodilator such as but not limited to nitroprusside, dantrolene, nifedipine, verapamil, phentolamine, tolazoline, procardia, or the like. It is preferable to use papaverine having a concentration of from about $1 \times 10E-4$ to about $30 \times 10E-4M$, more preferably about $3 \times 10E-4M$. This media solution also has certain additives: bicarbonate, HEPES or similar buffer, glutamine, D-glucose and sodium pyruvate.

Before the vessel is completely removed, the stopcock ends are attached to the support track 14 of the stent apparatus 10 in order that the vessel does not have the opportunity to contract. It is this natural contraction of the vessel that is deleterious to the inner endothelial lining of the vessel and for which the stent is designed to protect. Once the remaining portions of the vessel are dissected, the stent 10 with the attached vessel is ready for transport in an outer container.

The stent 10 continues to provide support and protection for the vessel while progressing through other stages in the cryopreservation process. Upon arrival of the stented vessel for cryopreservation, the stent will provide the support for continued flushing and inspection for tying of collateral vessels. During the freezing process the stent will be the support necessary to prevent the vessel side walls from collapsing and at the final phase during thawing and dilution the stent again keeps the vessel from collapse and facilitates the addition and removal of cryoprotectant agents.

The present invention provides a method of freezing, storing and thawing endothelial lined tissue, such as a vein and artery. The tissue that is frozen according to the present invention can be stored for long periods of time at ultra cold temperatures with minimal loss of cell viability. The present invention includes a unique freezing profile that allows a tissue such as vein and artery to be frozen down to the temperature of liquid nitrogen, approximately $-196°$ C., with minimal tissue damage due to ice crystal formation or solution effects due to slow cooling. The present invention also includes a thawing schedule whereby the frozen tissue can be rapidly thawed with minimal tissue damage. Veins and arteries that are cryopreserved according to the present invention are biologically viable when thawed and are ideally suited for replacing diseased or mechanically damaged vessels.

The tissue to be preserved is only as good as that which is received into the laboratory. Consideration must be given to donor age, health and history of vascular disease. Another important consideration is the time between death and the harvest of the vessels (warm ischemia) and the time from the harvest of the vessels to laboratory processing (cold ischemia). Attention must be paid to the method of handling the tissue during procurement and the medium used to ship the tissue.

A donor that can be used as a source of human vessels which are frozen according to the present invention should be in the age range of up to about 55 years of age and the donor should not have suffered from significant atherosclerosis, diabetes, circulatory disorders, severe hypertension, varicose veins, or communicable disease.

All procurement is to be performed under sterile conditions. Time delay between death and harvest will have a deliterious effect on the endothelial cell layer and therefore should be completed immediately after expiration of the donor but in any case not longer than about 10 hours post mortem. For example, the ideal length for coronary bypass procedure would be to procure a vessel of approximately 17 cm with at least a diameter of 4 mm. It is to be understood that other diameters and lengths are usable and are within the scope of this invention.

Sterilization

It was discovered that many antibiotics were extremely toxic to the endothelial layer of the vessels. This toxicity is the result of a number of factors including time, temperature and mode of action. In addition to the antibiotics, the antimycotic (antifungal) agents may be deleterious to the tissue endothelium. It is important to continually test new antibiotics and fungicides for cell toxicity and sterilization efficacy, in order to improve cell viability and kill microbes resistant to previous agents.

A mixture of an antibiotic and an antimycotic were found to provide suitable sterilization results. A mixture of Imipenem and Ancoban were found to be particularly suitable. Table 1 shows the effect of antibiotic incubation on endothelial viability in vitro.

TABLE I

| Effect of Antiobiotic Incubation on Endothelial Viability In Vitro | | |
|---|---|---|
| Antibiotic | Time | Significance |
| APCVL | 4 hrs. | NS* |
| Imipenem + gentamycin | 4 hrs. | NS |
| APCVL | 12 hrs. | $P < .05$ |
| PSA | 12 hrs. | NS |
| Imipenem + gentamycin | 12 hrs. | $P < .05$ |
| Imipenem − without gentamycin | 12 hrs. | NS |

TABLE I-continued

| Effect of Antiobiotic Incubation on Endothelial Viability In Vitro | | |
|---|---|---|
| Antibiotic | Time | Significance |
| Imipenem + Ancoban | 18 hrs. | NS |

*NS = Not Significant
APCVL = Amphotericin B, 25 micrograms/ml,
Polymixin B Sulfate, 100 micrograms/ml
Cefoxitin, 240 micrograms/ml
Vancomycin, 50 micrograms/ml
Lincomycin, 120 micrograms/ml
PSA = Penicillin (50 IU/ml)
Streptomycin (50 mg/ml)
Amphotericin B (10 mg/ml)

Freezing Media

The medium in which the tissue is frozen is of great importance for maintaining a balanced cell environment. Time and temperature also contribute to whether a particular medium will be successful. Generally, a protein suspension, such as blood serum or artifical serum, must also be present for maximum cell viability.

A number of freezing media can be successfully used in practicing the present invention. Media, such as balanced tissue culture medium or simple phosphate buffered saline, can be used for most tissue types. For this particular tissue type DMEM is the preferred medium with the associated additive components discussed previously.

The freezing media is composed of the enriched DMEM plus FCS from about 1% to 30%, more preferably 10% fetal calf serum; plus the range of papaverine discussed above, preferably about 0.012% papaverine; and chondroitin sulphate having a concentration of from about 1% to 10%, preferably 2.5% to 5%, more preferably 2.5%.

Dimethylsulphoxide ("DMSO") is also added either in at least one step of 1M or preferably in three steps of 0.25M, 0.5M and 1M titrations at 4° C. Concentrations of DMSO can range from about 0.5 to 3 molar. The increase in molarity of DMSO should preferably be gradual so as not to traumatize the blood vessel. DMSO can be added at higher temperatures but timing becomes far more critical and toxicity may result in some tissues.

An important innovation in endothelial protection used to further refine and preserve tissue is to use chondroitin sulfate. This glycosaminoglycan (GAGS) is a major component of the extracellular matrix. The molecular weight of chondroitin sulfate can vary from 5,000 to 50,000 and it is a sulphated dissacharide consisting of repeat units of D-glucuronic acid and N-acetyl-D-galactosamine. Currently, this material is an additive in K-sol, a solution used for the short term (4° C.) storage of corneas.

Examples of other suitable glycosaminoglycans include but are not limited to hyaluronic acid, dermatan sulfate, heparin sulfate, heparin, and the like. Other cryoprotectants include but are not limited to glycerol, polyvinylpyrolidone, hydroxyethyl starch, and polyethylene glycol, dimethylformamide, ethyl glycol, and the like.

Table II shows a series of experiments using this additive to the freezing solution. Groups 1-6 used a protocol which differed from Groups 7 and 8 in that a two hour 37° C. incubation was performed. The result indicate that the addition of chondroitin sulfate to the freeze mixture significantly improved endothelial viability.

These materials can be used in cryopreservation procedures with or without the stent apparatus 10. As a cryoprotectant chondroitin sulfate or its alternatives(-GAGS) can be employed in procedures for cryoprotection of cells, tissues and organs in addition to blood vessels.

TABLE II

Influence of Chondroitin Sulphate upon Endothelial Cell Viability

| Chondroitin sulfate (CS) addition (2.5 g %) †† | (reps) | T | Signif | Cell Viability (Regression) T-test | | Treated/Control Regression |
|---|---|---|---|---|---|---|
| | | | | Control | Treated | |
| 1) Without vs with chondroitin sulfate | 6 | 3.309 | ** † | (42) 51 | (124) 174 | 2.95 |
| a) Saphenous veins only | 3 | 3.426 | * | (147) 95 | (391) 429 | 2.66 |
| b) Femoral veins only | 3 | 4.091 | * | (25) 29 | (61) 71 | 2.44 |
| 2) Without vs with CS in mannitol during dilution (no CS during freeze) | 4 | .457 | ns | (217) 203 | (187) 171 | 86 |
| 3) Without vs with CS during 2 hr incubation (with CS during freeze and dilution) | 5 | .992 | ns | (109) 63 | (60) 47 | 55 |
| a) Saphenous veins only | 3 | .606 | ns | (94) 85 | (89) 71 | 95 |
| b) Femoral veins only | 2 | .603 | ns | (83) 40 | (30) 30 | .36 |
| 4) Unfrozen vs frozen without CS, with CS during dilution and 2 hr incubation | 4 | 12.171 | ** | (300) 327 | (57) 56 | .19 |
| 5) Without vs with CS during all steps except no CS during freeze | 6 | 2.069 | ns | 69) 48 | (32) 28 | 46 |
| 6) Unfrozen vs with CS during dilution, no CS during freeze and no incubation | 2 | 5.752 | ** | (390) 457 | (177) 163 | 45 |
| Alternative CS Concentrations | | | | | | |
| 7) Without vs with 10 g % chondroitin sulfate (CS) | 4 | 2.415 | * | (118) 172 | (319) 334 | 2.70 |
| 8) Without vs w/1 g % | 4 | 1.704 | ns | (207) 131 | (69) 82 | 33 |

TABLE II-continued
Influence of Chondroitin Sulphate upon Endothelial Cell Viability

| Chondroitin sulfate (CS) addition (2.5 g %) | (reps) | T | Signif | Cell Viability (Regression) T-test Control | Treated | Treated/Control Regression |
|---|---|---|---|---|---|---|
| chondroitin sulfate | | | | | | |

† ns = not significant; (P > .05); * ≦ P .05; ** ≦ P .01
†† Groups 1-6 were performed using Protocol II. Protocol II differed from Protocol I by the addition of post-thaw 2 hr. 37° C. incubation in culture medium

Freeze Profile

The freezing profile is of critical importance to successful cryopreservation of a tissue. A multitude of variables exist to maximize tissue survival. For instance, the volume of fluid, the size of the tissue, geometry of the package and the combination of characteristics incorporating cryoprotectant, tissue, and freezing media all contribute to an optimal freezing profile. It is to be understood that the prior art freezing profiles available for cell suspensions may not be suitable for freezing blood vessels, and that prior art freezing profiles for heart valve tissue also may not be suitable. It has been determined that each tissue has its own unique and optimal freezing profile. The freezing profile required to successfully cryopreserve one tissue may be different from the freezing profile required to successfully cryopreserve another tissue.

A number of factors need to be considered when freezing a tissue. Among these factors are: the temperature around the equilibrium point, (generally +4° C., to the temperature at the freezing point); release and control of the exothermic heat given off at the freezing point; optimum cooling rate as which is determined by the permeability of the cell membrane to water; the surface to volume ratio of the cells; the type and concentration of cryoprotective agents in the media; temperature and time of exposure to those agents, cooling rate removal of the cryopreserved tissue from the controlled rate freezer and immersing the tissue into a liquid nitrogen refrigerator, and, warming rate and the thickness of the tissue.

Detail of Freezing Profile

Thus, the method of harvesting veins from a donor, placing the vessel into a medium with the proper tissue preserving characteristics for transportation, and the use of proper cryopreservation agents prior to the freezing of the vessel according to a freezing schedule is desirable for proper cryopreservation. To accomplish this the chamber temperature and cooling rate is controlled so as to produce the desired effect on the sample. Since the blood vessel tissues cool at slightly different rates, and phase changes occur at particular temperatures, careful control over the rates of freezing should be maintained.

Figure 3:
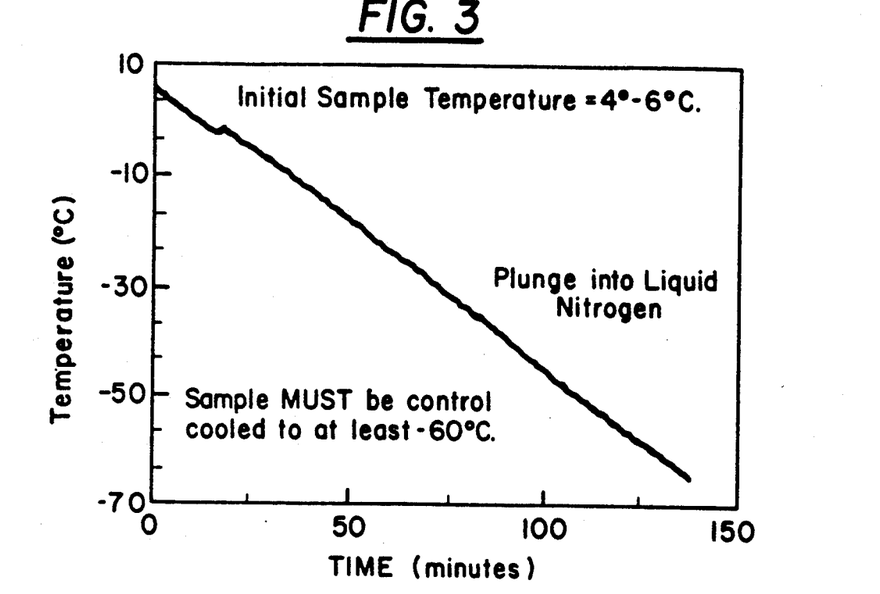
FIG. 3 is a schematic representation of a freezing profile for freezing a vein.

The range of the freezing rate is also a function of the fluid volume in the package containing the blood vessel as well as the geometry of the package. While the freezing profiles described herein are related to the volume and geometry of the package, it is to be understood that the present invention encompasses those modifications of package design which result in a change in the volume and geometry, which in turn, result in a variance in the freezing rate. Freezing rates can vary to a certain amount at a given temperature. A suitable range is from about 0.01°-100° C./min, about 0.1°-30° C./min, preferably about 0.3°-1° C./min and more preferably 0.5°-1° C./min. In a preferred embodiment of the present invention, the overall rate of freezing of the blood vessel is kept at approximately 0.5° C. per minute. A preferred freezing schedule used to cryopreserve the veins and arteries in the present invention is comprised of placing the packaged tissue, having a total volume of about 2.5 cm×25 cm, into a freezing apparatus. A typical profile for a specific fluid volume of 75-85 ml would have the initial temperature of the chamber set to −10° C. The chamber is set to cool at a rate of 0.01° C./min. until the sample(s) reaches +4° C. At this point the tissue cools at a rate of 0.5±0.2° C./min. until the sample reaches −2±0.5° C., at which time a phase change is initiated. At this point, in order to prepare for the exothermic heat of fusion, the cooling rate is increased to −30° C. until the chamber reaches −70° C. Immediately after the chamber reaches −70° C., the chamber is warmed at a rate of 20° C./min. until the chamber reaches −60° C., whereupon this temperature is held for a period of 17 minutes. During this time, the actual rate of vessel cooling is approximately −0.5 ±0.2° C./min. At the end of this 17 minutes period, the chamber is again warmed at a rate of 10° C./min. until the chamber reaches a level of −30° C. The level of −30° C. is held for one minute and then the cooling of the chamber commences at a rate of 0.01° C./min. until the sample reaches −20° C. During this time, the actual rate of cooling of the sample is approximately 0.5±0.2° C./min. The final rate adjustment step is to continue cooling at 0.5±0.2° C./min. until the sample reaches −65° C. or below. The result of this freezing profile is a rate of freezing from the start of the procedure until the end of about 0.5±0.2° C./min. This rate of cooling has been optimized for vein tissue. The package containing the vein is removed from the chamber and placed in the storage liquid nitrogen refrigerator at −196° C. FIG. 3 illustrates a typical freeze profile of the present invention.

At such time that the vessel is requested by an implanting institution, the tissue will remain in the liquid nitrogen refrigertor.

Shipping

At the request of the implanting hospital, the tissue may be returned in a suitable insulated shipping container such as the container disclosed in U.S. Pat. No. 4,597,266 which is incorporated by reference in its entirety herein, which includes a cardboard container with four inches of foam insulation. A preferred embodiment is the use of dry ice which has been stored in liquid nitrogen whereupon liquid nitrogen infused dry ice is placed around the package containing the vessel. The package is then placed into the box. Appropriate protocols and other papers necessary to document clinical implants are included in the shipment.

Upon arrival at the hospital, the vessel and its associated package are placed into a liquid nitrogen freezer.

The tissue cannot tolerate storage at temperatures above 130° C. since repeated cycling of temperatures has a tendency to lessen the viability of the cells. Storage at temperatures equivalent to dry ice (−78.6° C.) is not considered sufficiently cold to prevent enzyme molecular degradation of the tissue and thus the storage time is significantly reduced.

Thawing

The thawing and diluting steps with an allograft must be clearly defined, since ice crystal growth and osmotic shock can still harm the tissue. Venous blood vessels should be thawed by being placed in a warm water bath. It has been determined that a thawing rate of 1°–1000° C./min., preferably, 10°–50° C./min. is appropriate for these vessels, depending upon the volume of the sample. Once thawed, the cryoprotectant of choice must be removed, usually in a step-wise fashion, to lessen the effects of osmotic shock to the cells and thus allow for an orderly equilibration of the cell with the surrounding medium. Time and temperature are major considerations.

Immediately prior to the time that the vessel is to be used, it is to be thawed and the cryopreservation additives are to be removed using a gradual dilution procedure to minimize osmotic damage. This thawing and dilution procedure is considered as important as the actual freezing procedure since ice crystal formation can occur during this phase of the procedure as well. In addition, inattention to proper temperature and timing can and will either reduce the number of viable cells due to the toxicity of the cryoprotectant ingredients and can on occasion actually lead to the cracking of the vessels into unusable pieces.

The following specific examples will illustrate the method of the present invention as it applies to harvesting, freezing to ultra-cold temperatures, and thawing of a blood vessel. It will be appreciated that the example will be apparent to those of ordinary skill in the art and that the invention is not limited to this specific illustrative example.

EXAMPLE 1

The dissection is performed using sterile "no-touch" technique. The vessel and adventitia are bathed in perfusion medium (DMEM, 10% fetal calf serum and 0.12 mg of papaverine/ml) throughout the procedure. This medium also has as an additive: 25 mmol Hepes buffer, glutamine, 1000 mg D glucose/L and sodium pyruvate at pH 7.3±0.5(GIBCO Lab Cat. #380-2320). Following removal of the adventitia, a caudal venotomy is made and the stopcock assembly is inserted and ligated into place. The vessel is gently perfused with the perfusion medium. The collateral vessels are identified and ligated approximately 1-2 mm from the main vessel.

Before complete excision of the vessel, the support track 14 of the stent apparatus 10 is affixed to the distal and proximal stopcock assemblies 18 and 22. The dissection is completed, the proximal stopcock is closed and the vessel is infused with the perfusion medium up to approximately 100 mmHg, whereupon the distal stopcock is closed in order to keep the vessel distended. The vessel with the remaining perfusion solution is placed into a shipping container such as a plastic tube and double sterile wrapped. The transportation box is commonly made of styrofoam and the tube containing the vessel is placed in water and ice at approximately 4° C. Hereafter, a courier service is commonly used to speed the delivery to the laboratory, since the vessel, in order to remain living, should arrive within about 24 hours after the cessation of the donor heartbeat.

Upon arrival at the processing laboratory, the vessel is checked for proper packaging to verify that ice is still present. In a clean room, a sterile field is established to inspect the vessel and complete the processing steps, the first of which is to inspect and trim extraneous tissue. After all collateral branches have been checked and there are no leaks, the stented vessel is ready to start antibiotic sterilization.

Sterilization In order to prophylactically sterilize the vessels, the following critical procedure must be observed.

1. Imipenem (12 $\mu$g/ml) is placed into a solution of DMEM, which is a tissue culture media;
2. Ancoban (antimycotic) (50 $\mu$g/ml) is also added to the solution;
3. the vessel is perfused and bathed in this solution is placed into a 37° C. incubator for four hours.

Following the titration of the cryoprotectant, the vessels are packaged in pouches which are capable of withstanding the rigors of ultra cold cryopreservation. Normally, several successive layers of packaging are used in order to preserve sterility of the inner package containing the vessel. Finally, the vessel is ready for cryopreservation.

The freezing medium is composed of the enriched DMEM10% fetal calf serum+0.12 mg/ml papaverine+2.5% chondroitin sulphate+ IM DMSO or other suitable protectant.

Detail of Freezing Profile

The freezing schedule used to cryopreserve the veins and arteries in the present invention is comprised of placing the packaged tissue with 75-85 ml of fluid volume and cylindrical shape of 2.5 cm×25 cm into a suitable freezing apparatus (such as Cryomed Model #1010 (990C)). Temperatures provided are approximate and a certain amount of latitude must be provided to account for machine and instrument variance. The initial temperature of the chamber is set to 10° C. The chamber is set to cool at a rate of 0.01° C./minute until the sample reaches +4° C. At this point the tissue cools at a rate of 0.3°±0.2° C./min. until the sample reaches −2° C., which initiates a phase change. At this point, in order to prepare for the exothermic heat of fusion, the cooling rate is increased to −30° C. until the chamber reaches −70° C. Immediately after the chamber reaches −70° C., the chamber is warmed at a rate of 20° C./min. until the chamber reaches −60° C., whereupon this temperature is held for a period of 17 minutes. During this time, the actual rate of vessel cooling is approximately 0.5°±0.2° C./min. At the end of this 17 minute period, the chamber is again warmed at a rate of 10° C./min. until the chamber reaches a level of −30° C. The level of −30° C. is held for one minute and then the cooling of the chamber commences at a rate of 0.01° C./min. until the sample reaches −20° C. During this time, the actual rate of cooling of the sample is approximately 0.5°±0.2° C./min. The final rate adjustment step is to continue cooling at 0.5°±0.2° C./min. until the sample reaches −65° C. or below. The result of this freezing profile is a rate of freezing from the start of the procedure until the end of 0.5°±0.2° C./min. This rate of cooling has been optimized for vein tissue. The package containing the vein is removed from the chamber and placed in the storage liquid nitrogen refrigerator at −196° C.

Until such time that the vessel is requested by an implanting institution, the tissue will remain in the liquid nitrogen refrigerator.

Shipping

The frozen vessel is shipped in an appropriate container in the manner as described above.

Thawing

The thawing and dilution procedure can be performed as follows:

1. In a sterile field and with all sterile components, at least two liters of sterile water warmed to about 37°–42° C. are placed into an instrument tray or other vessel to accommodate the length of the stented tissue.

2. The packaged vessel is removed from the protective cardboard box and placed into the water bath. The package is to remain in this bath, where it is manually or automatically agitated for approximately eight minutes, or until such time that gentle palpation of the package reveals that no further ice crystals are present.

3. Once it has been determined that no ice crystals are present, the package is removed from the bath and the outer foil package is carefully wiped dry in the area between the two notches and with a pair of scissors, the foil package is cut between the two notches. Sterile forceps are used to retrieve the inner clear pouch from the foil pouch and the process is repeated using sterile scissor to cut the inner pouch.

4. The stented vessel is carefully removed and placed into a clean sterile instrument tray or other suitable container whereupon the first of the dilution steps takes place. A syringe is used to add to the vessel 50 cc of a solution ("Bottle A") containing:
0.5M mannitol;
10% fetal calf serum; and
DMEM.
The vessel is gently perfused with this solution and the washout material is allowed to rest in the tray whereupon the vessel is allowed to soak for five minutes. Instead of mannitol, any non-permeable biocompatible sugar can be substituted, such as but not limited to, sucrose, sorbitol, trehalose, glucose or the like. The dilution of DMSO concentration should be in decreasing steps of no more than ½ the molarity of the previous step. Thus, if the original DMSO concentration is 1M, the first dilution step should be ½M sugar, followed by ¼M sugar and finally zero molar sugar.

5. At the completion of step 4, the solution in the tray is discarded into another suitable container and the following is added to the tray and mixed:
50 cc remaining in the bottle A from step 4; plus 50 cc from a solution ("Bottle B") containing:
10% fetal calf serum; and
DMEM
The mixture is now 0.25M mannitol. A syringe is used to gently perfuse the vessel with this mixture, and it is bathed in this solution for approximately 5 minutes.

6. At the completion of step 5, the contents of the tray are again discarded and the remainder of bottle B is added to the tray. The vessel is gently perfused and agitated in this solution for five minutes.

7. The vessel is now ready for transplant, but should not be removed from the stent until just prior to its intended use.

Figure 4:
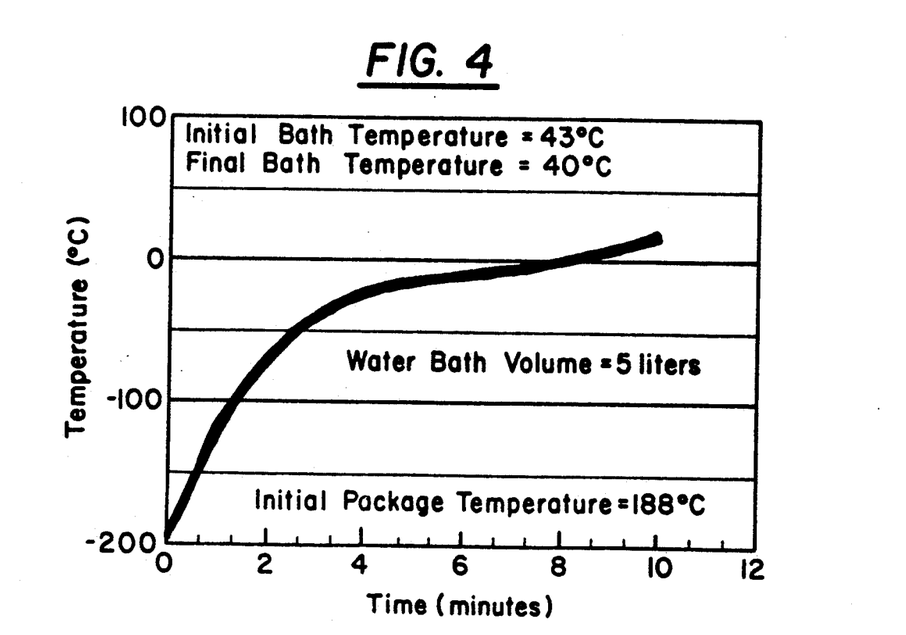
FIG. 4 is a representation of a thawing curve for a stented vein in approximately 80-90 ml of solution according to a preferred embodiment of the present invention.

FIG. 4 illustrates a typical thawing curve based upon an 85 ml (1M DMSO+DMEM) sample containing 20 cm. segment of vein being placed in 5 liters of 42° C. water and package was agitated by hand twice per minute for 15 seconds for each agitation until the vessel is thawed. The water bath was allowed to cool as the thaw progressed. The thawing rate was approximately 25° C./min. A typical thawing time is about eight minutes.

Transplant

The vessels preserved by the method just described are intended for use as arterial substitutes for the coronary arteries or for peripheral vascular reconstruction. Accordingly, since the graft tissue is antigenic tissue several precautions and recommendations are suggested:

1. The donor/recipient blood groups should be compatible;

2. A postoperative course of antiplatelet therapy may include but not be limited to Dipyridamole or aspirin; and 3. Low dose short duration immunosuppression which may include but not be limited to cyclosporin, prednisolone, and azathioprine to minimize the possibility of graft rejection. By use of the above technique, platelet deposition is depressed, thus lessening the possibility for thrombus formation and eventual loss of patency. Other forms of vessel pretreatment to lessen immunologic effects such as incubation in an immunosuppressive agent could be considered.

Studies to Support the Claim that Vessel Endothelial Cells are Preserved

An endothelial cell line was comprised of clonal bovine endothelium (BFA-1c). These cells were cryopreserved in situ while attached to plastic tissue culture substrate. Viability was determined by using a combination of acridine orange and propidium iodide, a dye inclusion/exclusion assay. Dimethylsulfoxide was found to be more effective than other cryoprotective agents tested including glycerol, hydroxyethyl starch and polyvinlprolidone. It was determined that 1M DMSO was optimal when used in combination with slow cooling rates. See Table III.

TABLE III

Studies on Freezing Procedures for Veins
(using limiting dilution assay on endothelial cells)

| Freezing rates | reps | T | Signif[1] | 1 Cell Viability (Regression) T-test Control | Treated | Treated/Control Regression |
|---|---|---|---|---|---|---|
| 1) Unfrozen vs 0.5°/min, 3 step DMSO addition | 6 | 6.696 | ** | (258) 338 | (153) 138 | .59 |
| 2) Unfrozen vs 3°/min, 3 step DMSO addition | 3 | 3.554 | * | (248) 228 | (96) 56 | .39 |
| 3) 0.5° vs 3°/min, 3 step DMSO addition | 3 | 1.679 | ns | (119) 95 | (96) 56 | .81 |

TABLE III-continued

Studies on Freezing Procedures for Veins
(using limiting dilution assay on endothelial cells)

| Freezing rates | reps | T | Signif[1] | 1 Cell Viability (Regression) T-test | | Treated/Control Regression |
|---|---|---|---|---|---|---|
| | | | | Control | Treated | |
| 4) Without vs with DMSO 0.5°/min (3 step) | 3 | 4.512 | * | (20) 18 | (109) 84 | 5.45 |

[1]ns = not significant, p > 0.05
* = p ≦ .05
** = p ≦ .01

At 0.5° C./min., more than 70% of the endothelial cells survived, as compared with a cooling rate of 10° C./min. or more where less than 20% of the cells survived. See Table IV.

TABLE IV

| Influence of Cooling Rate Upon Survival of a Bovine Endothelial Cell Line Cooling Rate °C./min | | | | |
|---|---|---|---|---|
| Experiment # | 1 | 3 | 10 | 30 |
| Viable Cells 1 | 68.8 | 58.7 | 17.5 | 15.3 |
| (% Total) 2 | 78.9 | 63.1 | 3.1 | 16.1 |
| 3 | 76.7 | 56.4 | 17.5 | 10 |
| 4 | 80.3 | 28.4 | 24.5 | 5.3 |
| Mean plus one | 75.68 | 51.65 | 15.65 | 11.68 |
| standard | +/− | + | +/− | +/− |
| deviation | 5.1 | 13.64 | 9.0 | 5.0 |

The previous experiment was repeated using actual saphenous vein vessels and utilizing the protocol for preparation and titration of the DMSO discussed earlier. In essence, DMSO is added in three steps of ten minutes each at 4° C., such that the concentration increase from ¼, ½ to 1M. The DMSO is mixed with DMEM containing 25 mM HEPES buffer and 10% fetal calf serum. The freezing rate was varied from either 0.5° or 3° C./min. The experiments show that the freezing rate of 0.5° C. resulted in a higher percentage of endothelial integrity than the faster rate of 3° C. See Table V.

TABLE V

| Endothelial Integrity After Cryopreservation at 0.5° or 3° C./min. | | | | |
|---|---|---|---|---|
| Rate | | | Endothelial Integrity (%) | |
| (°C./min) | Sample # | Vein # | Mean +/− se | % of Control |
| Control | 114 | 38 | 86 +/− 1 | — |
| 3 | 10 | 4 | 62 +/− 7 | 72.1 |
| 0.5 | 20 | 7 | 70 +/− 5 | 81.4 |

We claim:

1. A kit comprising:

(i) a blood vessel stent comprising
      first and second elongated stylets each having an end capable of insertion within a portion of a blood vessel from a donor;
      means on said stylets operative to engage the interior of the blood vessel and thereby facilitate fluid tight ligation of the blood vessel on the stylets; and
      support means receiving the stylets in selectively adjustable mutually confronting relation whereby the blood vessel is distended between the stylets to prevent contraction of the blood vessel, so that the stent supports the blood vessel through the stages of procurement and cryopreservation; and
   (ii) a composition comprising a cryoprotectively effective concentration of a cell penetrating cryoprotectant and a cryoprotectively effective concentration of a glycosaminoglycan.

2. The kit according to claim 1 wherein said glycosaminoglycan is chondroitin sulfate.

3. The kit according to claim 1 wherein said cell penetrating cryoprotectant is DMSO.

4. A kit for the cryopreservation of a blood vessel comprising:

(a) a blood vessel stent;
   (b) an effective amount of a cryopreservative solution comprising a mixture of:
      Delbecco's Minimum Essential Medium
      25 mmol hepes buffer,
      glutamine,
      1000 mg D-glucose/liter,
      sodium pyruvate at pH 7.3,
      10% fetal calf serum,
      0.012% papaverine,
      2.5% chondroitin sulfate,
      1M DMSO; and
   (c) packaging means for maintaining the sterility and integrity of the blood vessel.

* * * * *